US012569158B2

(12) United States Patent
Rakshit et al.

(10) Patent No.: US 12,569,158 B2
(45) Date of Patent: Mar. 10, 2026

(54) SYSTEMS AND METHODS FOR DETECTING ANOMALY IN BIOLOGICAL TISSUES

(71) Applicant: Tata Consultancy Services Limited, Mumbai (IN)

(72) Inventors: Raj Rakshit, Kolkata (IN); Anwesha Khasnobish, Kolkata (IN); Annesha Mazumder, Kolkata (IN); Arijit Chowdhury, Kolkata (IN); Tapas Chakravarty, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 59 days.

(21) Appl. No.: 18/903,637

(22) Filed: Oct. 1, 2024

(65) Prior Publication Data

US 2025/0169709 A1     May 29, 2025

(30) Foreign Application Priority Data

Nov. 23, 2023     (IN) .............................. 202321079723

(51) Int. Cl.
    *A61B 5/0507*        (2021.01)
    *G01S 13/89*         (2006.01)
(52) U.S. Cl.
    CPC ............ *A61B 5/0507* (2013.01); *G01S 13/89* (2013.01); *A61B 2562/0228* (2013.01)
(58) Field of Classification Search
    CPC .......... A61B 5/0507; A61B 2562/0228; G01S 13/89
    See application file for complete search history.

(56) References Cited

U.S. PATENT DOCUMENTS 4,247,815 A  *  1/1981  Larsen ................. A61B 5/0507
                                              324/692
11,426,080 B2 *  8/2022  Stang ................... A61B 5/0036
                    (Continued)

OTHER PUBLICATIONS

Ghasr, Mohammad Tayeb Ahmad et al., "Multimodal Solution for a Waveguide Radiating Into Multilayered Structures—Dielectric Property and Thickness Evaluation", Date: 2009, Publisher: Missouri University of Science and Technology, Link:https://scholarsmine.mst.edu/cgi/viewcontent.cgi?article=2746&context=ele_comeng_facwork.

(Continued)

*Primary Examiner* — Dixomara Vargas
(74) *Attorney, Agent, or Firm* — FINNEGAN, HENDERSON, FARABOW, GARRETT & DUNNER LLP

(57)                    ABSTRACT

The usage of microwave imaging for biomedical (BMWI) applications is still challenging due to the imprecise reconstruction of the relative permittivity of tissues and the ill-posed inverse scattering problem. Anomaly detection in biological tissues demand in-vivo, non-invasive, and non-contact measurements. Considering and proving the anomaly as a point object in the microwave imaging is erroneous and results in false implications about the anomaly's presence, location, and characteristics. Present disclosure provides systems and methods for anomaly detection in biological tissues. An intensity map of target region is generated to detect tumor. Area around the tumor is processed to obtain a refined image. As the tumor is embedded in tissues of higher dielectric constant, image thus formed is larger in size than actual tumor. An iterative numerical computation method is implemented to estimate relative permittivity. Subsequently, the effective size of the anomaly is approximately estimated, which is close to their actual values.

15 Claims, 6 Drawing Sheets receiving, at a Vector Network Analyzer (VNA), reflected microwaves projected on a duty under test (DUT) kept at an initial distance, by using antennas, the DUT comprises a biological tissue ~ 202 measuring, by using the VNA, a first reflection coefficient from reflected microwaves ~ 204 converting the first reflection coefficient to a time series data and filtering the time series data to obtain a filtered time series data ~ 206 applying a Delay-Multiply-and-Sum (DMAS) technique on the filtered time series data to generate a radar return image at a distance from a frontend of the antennas ~ 208 measuring a peak intensity from the radar return image ~ 210 obtaining an optimum distance by varying the distance at which the peak intensity is maximum ~ 212 computing a measured distance (MD) based on a comparison between the optimum distance and the initial distance ~ 214 measuring a second reflection coefficient specific to a first scenario and a third reflection coefficient specific to a second scenario ~ 216 iteratively performing
computing a permittivity for a plurality of frequencies based on a thickness of DUT, using the second reflection coefficient and the third reflection coefficient ~ 218a
performing a first comparison of the permittivity with a first threshold ~ 218b     ~ 218
performing a second comparison of a degree of the DUT with a convergence criteria ~ 218c
until a candidate effective permittivity for frequencies is obtained computing an effective permittivity (EP) based on the candidate effective permittivity computed for the frequencies ~ 220 computing at least one of an actual depth and an actual diameter of an anomaly in the biological tissue based on the MD and EP ~ 222

(56)          References Cited

U.S. PATENT DOCUMENTS

| 2003/0088180 | A1 | 5/2003 | Van Veen et al. |
| 2005/0107693 | A1 | 5/2005 | Fear et al. |
| 2006/0058606 | A1 * | 3/2006 | Davis ....................... A61B 5/05 |
| | | | 600/407 |
| 2018/0121580 | A1 | 5/2018 | Tsang |

OTHER PUBLICATIONS

Park, Won-Kwang, "Real-time microwave imaging of unknown anomalies via scattering matrix", Date: 2018, Publisher: Kookmin University, Link:https://arxiv.org/pdf/1809.05830.

* cited by examiner

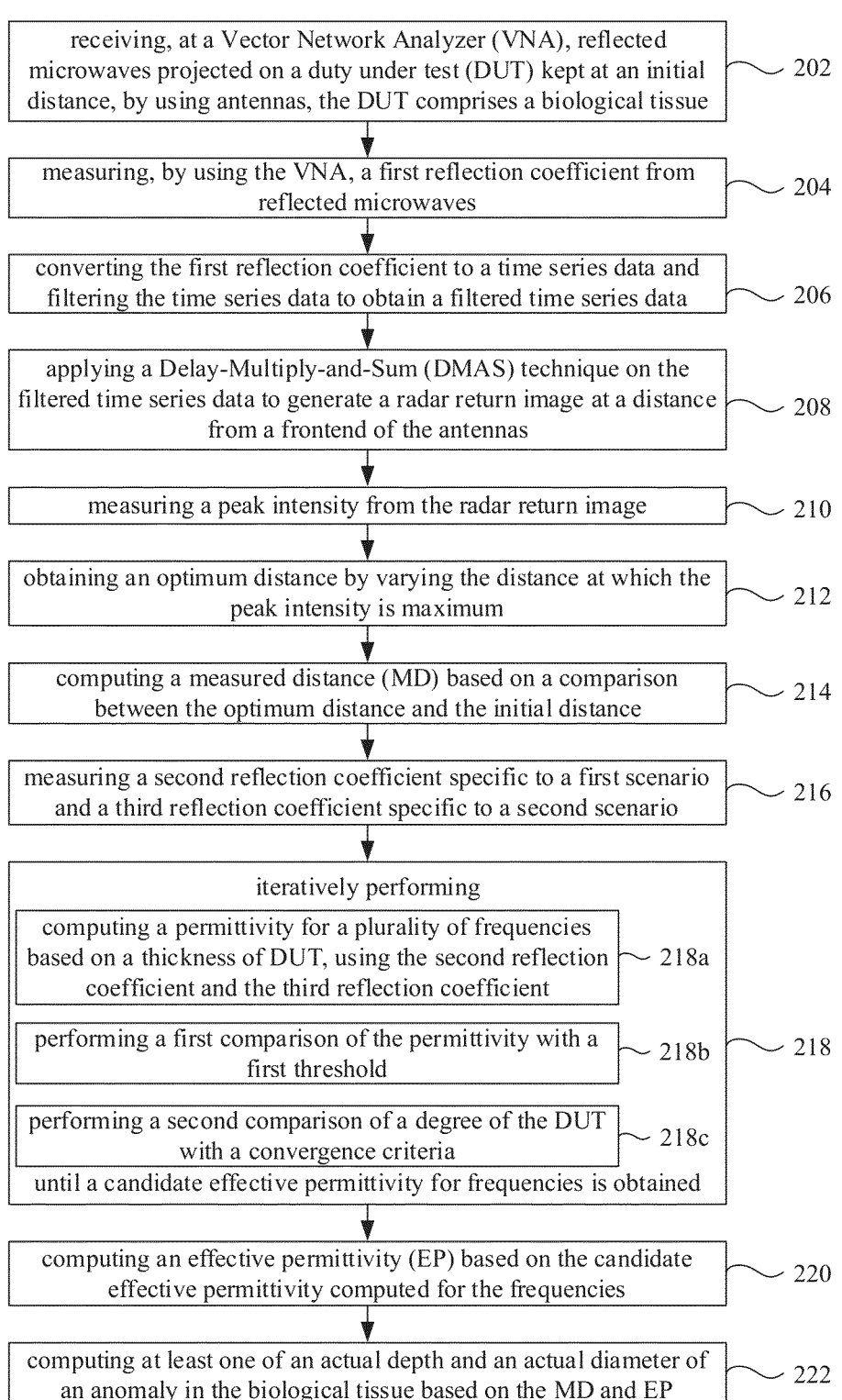

receiving, at a Vector Network Analyzer (VNA), reflected microwaves projected on a duty under test (DUT) kept at an initial distance, by using antennas, the DUT comprises a biological tissue ~ 202 measuring, by using the VNA, a first reflection coefficient from reflected microwaves ~ 204 converting the first reflection coefficient to a time series data and filtering the time series data to obtain a filtered time series data ~ 206 applying a Delay-Multiply-and-Sum (DMAS) technique on the filtered time series data to generate a radar return image at a distance from a frontend of the antennas ~ 208 measuring a peak intensity from the radar return image ~ 210 obtaining an optimum distance by varying the distance at which the peak intensity is maximum ~ 212 computing a measured distance (MD) based on a comparison between the optimum distance and the initial distance ~ 214 measuring a second reflection coefficient specific to a first scenario and a third reflection coefficient specific to a second scenario ~ 216 iteratively performing computing a permittivity for a plurality of frequencies based on a thickness of DUT, using the second reflection coefficient and the third reflection coefficient ~ 218a performing a first comparison of the permittivity with a first threshold ~ 218b          ~ 218 performing a second comparison of a degree of the DUT with a convergence criteria ~ 218c until a candidate effective permittivity for frequencies is obtained computing an effective permittivity (EP) based on the candidate effective permittivity computed for the frequencies ~ 220 computing at least one of an actual depth and an actual diameter of an anomaly in the biological tissue based on the MD and EP ~ 222

FIG. 2

SYSTEMS AND METHODS FOR DETECTING ANOMALY IN BIOLOGICAL TISSUES

PRIORITY CLAIM

This U.S. patent application claims priority under 35 U.S.C. § 119 to: Indian Patent Application No. 202321079723, filed on Nov. 23, 2023. The entire contents of the aforementioned application are incorporated herein by reference.

TECHNICAL FIELD

The disclosure herein generally relates to anomaly detection, and, more particularly, to systems and methods for detecting anomaly in biological tissues.

BACKGROUND

Microwave imaging (MWI) is an emerging field of medical imaging which is advantageous in certain terms compared to existing standard medical imaging modalities. However, there are existing problems with quantitative microwave imaging in biomedical domain. For instance, biological tissues are non-homogeneous, with varying dielectric properties of each tissue type. Application of microwave imaging method in biomedical domain is still challenging due to the imprecise reconstruction of the relative permittivity of tissues and the ill-posed inverse scattering problem. Estimating the relative permittivity of the tissues is challenging as abnormality is embedded.

SUMMARY

Embodiments of the present disclosure present technological improvements as solutions to one or more of the above-mentioned technical problems recognized by the inventors in conventional systems.

For example, in one aspect, there is provided a processor implemented method for detecting anomaly in biological tissues. The method comprises receiving, at a Vector Network Analyzer (VNA), one or more reflected microwaves projected on a duty under test (DUT) kept at an initial distance, by using one or more antennas, wherein the DUT comprises a biological tissue; measuring, by using the VNA, a first reflection coefficient from the one or more reflected microwaves; converting the first reflection coefficient to a time series data and filtering the time series data to obtain a filtered time series data; applying a Delay-Multiply-and-Sum (DMAS) technique on the filtered time series data to generate a radar return image at a distance d from a frontend of the one or more antennas; measuring a peak intensity from the radar return image; obtaining an optimum distance by varying the distance at which the peak intensity is maximum; computing a measured distance based on a comparison between the optimum distance and the initial distance; measuring, by using the VNA, a second reflection coefficient specific to a first scenario and a third reflection coefficient specific to a second scenario; iteratively performing: computing a permittivity for a plurality of frequencies based on a thickness of DUT, using the second reflection coefficient and the third reflection coefficient; performing a first comparison of the permittivity with a first threshold; and performing a second comparison of a degree of the DUT with a convergence criteria, until a candidate effective permittivity for each of the plurality of frequencies is obtained based on the first comparison and the second comparison; computing an effective permittivity based on the candidate effective permittivity computed for each of the plurality of frequencies; and computing at least one of an actual depth and an actual diameter of an anomaly in the biological tissue based on the measured distance and the effective permittivity.

In an embodiment, the step of filtering the time series data to obtain the filtered time series data is based on a second threshold.

In an embodiment, the second threshold is a pre-configured threshold or an empirically determined threshold.

In an embodiment, the first scenario comprises measuring the second reflection coefficient without placing the DUT between the one or more antennas, and the second scenario comprises measuring the third reflection coefficient by placing the DUT between the one or more antennas.

In an embodiment, the step of computing the permittivity is based on an iterative search method.

In another aspect, there is provided a processor implemented system for detecting anomaly in biological tissues. The system comprises: a memory storing instructions; one or more communication interfaces; and one or more hardware processors coupled to the memory via the one or more communication interfaces, wherein the one or more hardware processors are configured by the instructions to: receive, at a Vector Network Analyzer (VNA), one or more reflected microwaves projected on a duty under test (DUT) kept at an initial distance, by using one or more antennas, wherein the DUT comprises a biological tissue; measure, by using the VNA, a first reflection coefficient from the one or more reflected microwaves; convert the first reflection coefficient to a time series data and filtering the time series data to obtain a filtered time series data; applying a Delay-Multiply-and-Sum (DMAS) technique on the filtered time series data to generate a radar return image at a distance d from a frontend of the one or more antennas; measure a peak intensity from the radar return image; obtain an optimum distance by varying the distance at which the peak intensity is maximum; compute a measured distance based on a comparison between the optimum distance and the initial distance; measure, by using the VNA, a second reflection coefficient specific to a first scenario and a third reflection coefficient specific to a second scenario; iteratively perform: computing a permittivity for a plurality of frequencies based on a thickness of DUT, using the second reflection coefficient and the third reflection coefficient; performing a first comparison of the permittivity with a first threshold; and performing a second comparison of a degree of the DUT with a convergence criteria, until a candidate effective permittivity for each of the plurality of frequencies is obtained based on the first comparison and the second comparison; compute an effective permittivity based on the candidate effective permittivity computed for each of the plurality of frequencies; and compute at least one of an actual depth and an actual diameter of an anomaly in the biological tissue based on the measured distance and the effective permittivity.

In an embodiment, the filtered time series data is based on a second threshold.

In an embodiment, the second threshold is a pre-configured threshold or an empirically determined threshold.

In an embodiment, the first scenario comprises measuring the second reflection coefficient without placing the DUT between the one or more antennas, and the second scenario comprises measuring the third reflection coefficient by placing the DUT between the one or more antennas.

In an embodiment, the permittivity being computed is based on an iterative search method.

In yet another aspect, there are provided one or more non-transitory machine-readable information storage mediums comprising one or more instructions which when executed by one or more hardware processors cause detecting anomaly in biological tissues by receiving, at a Vector Network Analyzer (VNA), one or more reflected microwaves projected on a duty under test (DUT) kept at an initial distance, by using one or more antennas, wherein the DUT comprises a biological tissue; measuring, by using the VNA, a first reflection coefficient from the one or more reflected microwaves; converting the first reflection coefficient to a time series data and filtering the time series data to obtain a filtered time series data; applying a Delay-Multiply-and-Sum (DMAS) technique on the filtered time series data to generate a radar return image at a distance d from a frontend of the one or more antennas; measuring a peak intensity from the radar return image; obtaining an optimum distance by varying the distance at which the peak intensity is maximum; computing a measured distance based on a comparison between the optimum distance and the initial distance; measuring, by using the VNA, a second reflection coefficient specific to a first scenario and a third reflection coefficient specific to a second scenario; iteratively performing: computing a permittivity for a plurality of frequencies based on a thickness of DUT, using the second reflection coefficient and the third reflection coefficient; performing a first comparison of the permittivity with a first threshold; and performing a second comparison of a degree of the DUT with a convergence criteria, until a candidate effective permittivity for each of the plurality of frequencies is obtained based on the first comparison and the second comparison; computing an effective permittivity based on the candidate effective permittivity computed for each of the plurality of frequencies; and computing at least one of an actual depth and an actual diameter of an anomaly in the biological tissue based on the measured distance and the effective permittivity.

In an embodiment, the step of filtering the time series data to obtain the filtered time series data is based on a second threshold.

In an embodiment, the second threshold is a pre-configured threshold or an empirically determined threshold.

In an embodiment, the first scenario comprises measuring the second reflection coefficient without placing the DUT between the one or more antennas, and the second scenario comprises measuring the third reflection coefficient by placing the DUT between the one or more antennas.

In an embodiment, the step of computing the permittivity is based on an iterative search method.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 2 depicts an exemplary flow chart illustrating a method for detecting anomaly in biological tissues, using the system of FIG. 1, in accordance with an embodiment of the present disclosure.

DETAILED DESCRIPTION

Figure 1:
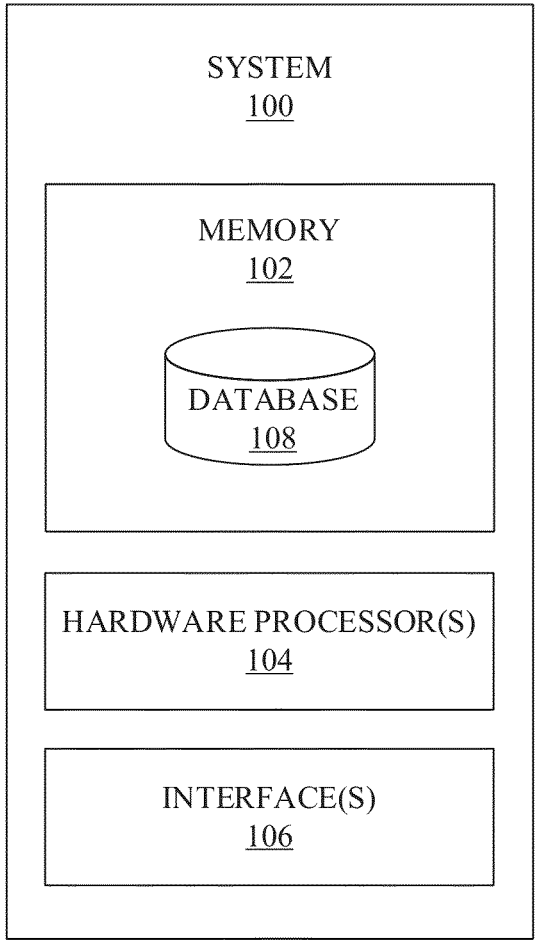
FIG. 1 depicts an exemplary system for detecting anomaly in biological tissues, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

The usage of microwave imaging for biomedical (BMWI) applications is still challenging due to the imprecise reconstruction of the relative permittivity of tissues and the ill-posed inverse scattering problem. Anomaly detection in biological tissues demand in-vivo, non-invasive, and non-contact measurements. The biological tissues are non-homogeneous, with varying dielectric properties of each tissue type. It is extremely difficult to estimate the relative permittivity of the tissues in which the abnormality is embedded. Moreover, existing works do not consider the enlarged dimension of the anomaly in the tissues obtained from the microwave imaging. Considering and proving the anomaly as a point object in the microwave imaging is erroneous and results in false implications about the anomaly's presence, location, and characteristics.

Embodiments of the present disclosure provide systems and methods for anomaly detection in biological tissues in the BMWI framework. The focus of the present disclosure is in distinguishing normal and anomalous tissues using an iterative search based numerical approach. An intensity map of a target region is generated to detect the tumor. Then the area around the tumor is further processed to obtain a refined image. As the tumor is embedded in tissues of higher dielectric constant, the refined image thus formed is usually larger in size than the actual tumor. Thus, to estimate the accurate size of the tumor (or anomaly), the system of the present disclosure implements an iterative numerical computation method to estimate relative permittivity ($\varepsilon$r). Subsequently, the effective size of the anomaly is approximately estimated, which is close to associated actual values. In other words, the present disclosure provides systems and methods that depicts, detect, localize, and characterize the anomaly in terms of electromagnetic properties from the generated microwave image. More specifically, the relative permittivity of the tissue is iteratively determined, which in-turn is utilized to obtain the dimensions of the anomaly more precisely.

Referring now to the drawings, and more particularly to FIG. 1 through 9, where similar reference characters denote corresponding features consistently throughout the figures, there are shown preferred embodiments and these embodiments are described in the context of the following exemplary system and/or method.

FIG. 1 depicts an exemplary system 100 for detecting anomaly in biological tissues, in accordance with an embodiment of the present disclosure. The system 100 may also be referred to as 'anomaly detection system' and interchangeably used herein. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is/are configured to fetch and execute computer-readable instructions stored in the memory. In an embodiment, the system 100 can be implemented in a variety of computing systems, such as laptop computers, notebooks, hand-held devices (e.g., smartphones, tablet phones, mobile communication devices, and the like), workstations, mainframe computers, servers, a network cloud, and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random-access memory (SRAM) and dynamic-random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information pertaining to duty under test comprising biological tissues. The database 108 further comprises various reflection coefficient from reflected microwaves obtained at a Vector Network Analyzer (VNA) using one or more antennas, radar return image, intensity values (low, medium, maximum, etc.), optimum distance, measure distance, permittivity, various thresholds, degree of the DUT, convergence criteria, candidate effective permittivity for all frequencies, effective permittivity, actual depth, actual diameter of anomaly in biological tissue, and the like. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

FIG. 2, with reference to FIG. 1, depicts an exemplary flow chart illustrating a method for detecting anomaly in biological tissues, using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, and the flow diagram as depicted in FIG. 2. Although process steps, method steps, techniques or the like may be described in a sequential order, such processes, methods, and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

At step 202 of the method of the present disclosure, the one or more hardware processors 104 receive, at a Vector Network Analyzer (VNA), one or more reflected microwaves projected on a duty under test (DUT) kept at an initial distance, by using one or more antennas. The DUT comprises a biological tissue.

Figure 3:
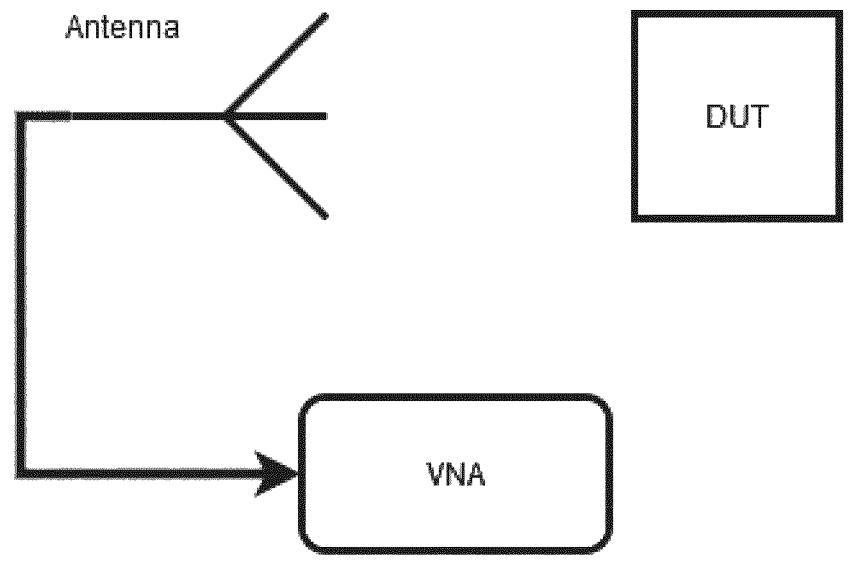
FIG. 3 depicts a setup for measuring the first reflection coefficient from the one or more reflected microwaves projected on a duty under test (DUT) kept at an initial distance (e.g., $d_{phy}$), by using one or more antennas, in accordance with an embodiment of the present disclosure.

At step 204 of the method of the present disclosure, the one or more hardware processors 104 measure, by using the VNA (or via the VNA), a first reflection coefficient from the one or more reflected microwaves. Using the VNA, the first reflection coefficient ($S_{11}$) is measured keeping duty under test (DUT) i.e., a rectangular wooden phantom with a hole in between. The hole is filled with (water) wet sponge at $d_{phy}$ distance in meters for a range of frequencies (freq) from the antenna frontend. Where $S_{11}$ is the reflection coefficient obtained acquired by the VNA. FIG. 3, with reference to FIGS. 1-2, depicts a setup for measuring the first reflection coefficient from the one or more reflected microwaves projected on a duty under test (DUT) kept at an initial distance (e.g., $d_{phy}$), by using the one or more antennas, in accordance with an embodiment of the present disclosure.

Figure 4:
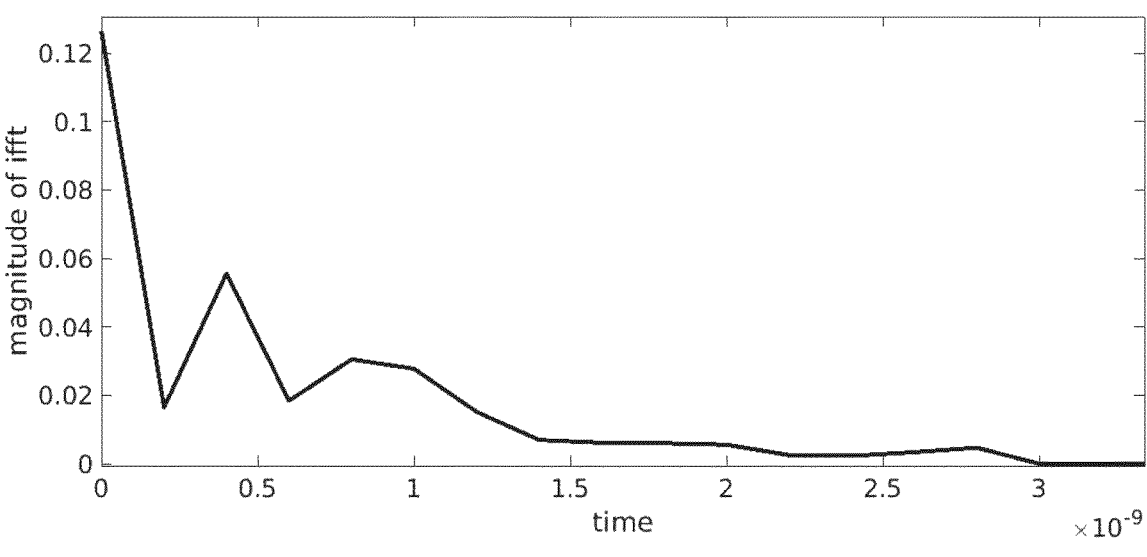
FIG. 4 depicts a graphical representation illustrating conversion of a first reflection coefficient to a time series data using an inverse fast fourier transform (ifft) and filtering the time series data to obtain a filtered time series data, in accordance with an embodiment of the present disclosure.

At step 206 of the method of the present disclosure, the one or more hardware processors 104 convert the first reflection coefficient to a time series data and filtering the time series data to obtain a filtered time series data. The filtered time series data is based on a second threshold. For instance, as per the experimentations conducted for the method of the present disclosure, time series data after 3 nano seconds were discarded to obtain the filtered time series data. Hence, the second threshold was 3 nano seconds in this case. FIG. 4, with reference to FIGS. 1 through 3, depicts a graphical representation illustrating conversion of the first reflection coefficient to a time series data using an inverse fast fourier transform (ifft) and filtering the time series data to obtain a filtered time series data, in accordance with an embodiment of the present disclosure. It is to be understood by a person having ordinary skill in the art or person skilled in the art that such conversion of the first reflection coefficient to the time series data using the inverse fast fourier transform (ifft) shall not be construed as limiting the scope of the present disclosure. In other words, the system and method of the present disclosure can employ any other known in the art transformation technique for the same. As can be seen from FIG. 4, range-gate data is at 3 nano-second i.e., discarding/filtering is performed for all data entries after 3 nana seconds (e.g., the second threshold). The second threshold is either a pre-configured threshold or an empirically determined threshold. For instance, if DUT is identical to previously performed experiments, they basis domain knowledge acquired while performing the method of the present disclosure, the second threshold can be pre-configured to same duration as cut-off. Otherwise, in other cases where the DUT is having a biological tissue not experimented prior, then the second threshold is identified basis trial and error method and may be empirically determined during the experimentation based on observations of the experimental run. It is to be understood by a person having ordinary skill in the art or person skilled in the art that value of the second threshold shall not be construed as limiting the scope of the present disclosure, and could vary depending upon the experimental setup's environment, DUT comprising biological tissue, and/or any other external factors/parameters affecting the DUT/method described herein.

Figure 5:
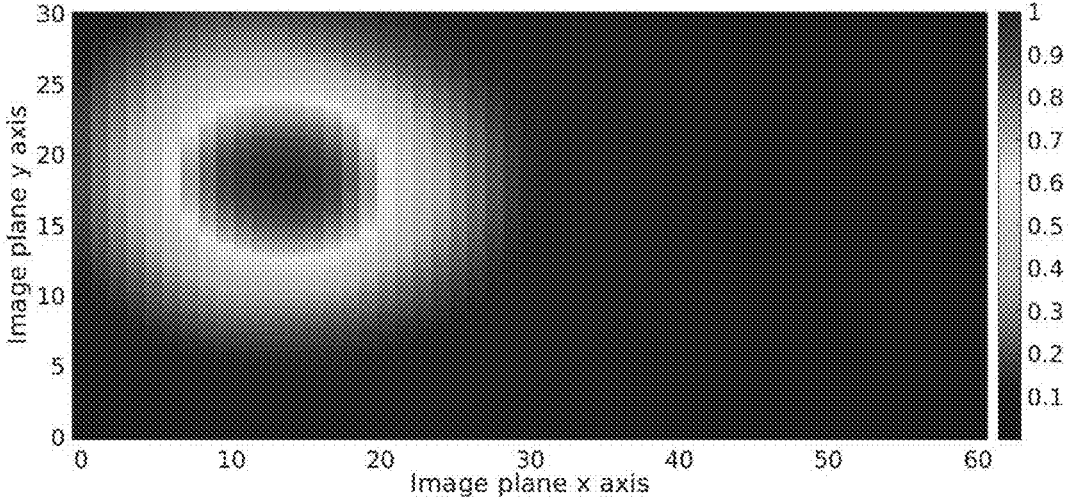
FIG. 5 depicts a radar return image upon applying a Delay-Multiply-and-Sum (DMAS) technique on the filtered time series data, in accordance with an embodiment of the present disclosure.

At step 208 of the method of the present disclosure, the one or more hardware processors 104 apply a Delay-Multiply-and-Sum (DMAS) technique on the filtered time series data to generate a radar return image at a distance (e.g., say distance 'd') from a frontend of the one or more antennas. FIG. 5, with reference to FIGS. 1 through 4, depicts a radar return image upon applying the Delay-Multiply-and-Sum (DMAS) technique on the filtered time series data, in accordance with an embodiment of the present disclosure. The DMAS technique/algorithm is applied on the filtered time series data and the radar return image is generated. The radar return image is generated using a colour coding of the image, in one example embodiment.

At step 210 of the method of the present disclosure, the one or more hardware processors 104 measure a peak intensity from the radar return image at the distance d from antenna frontend d≥$d_{phy}$ and the peak intensity is measured.

Figure 6:
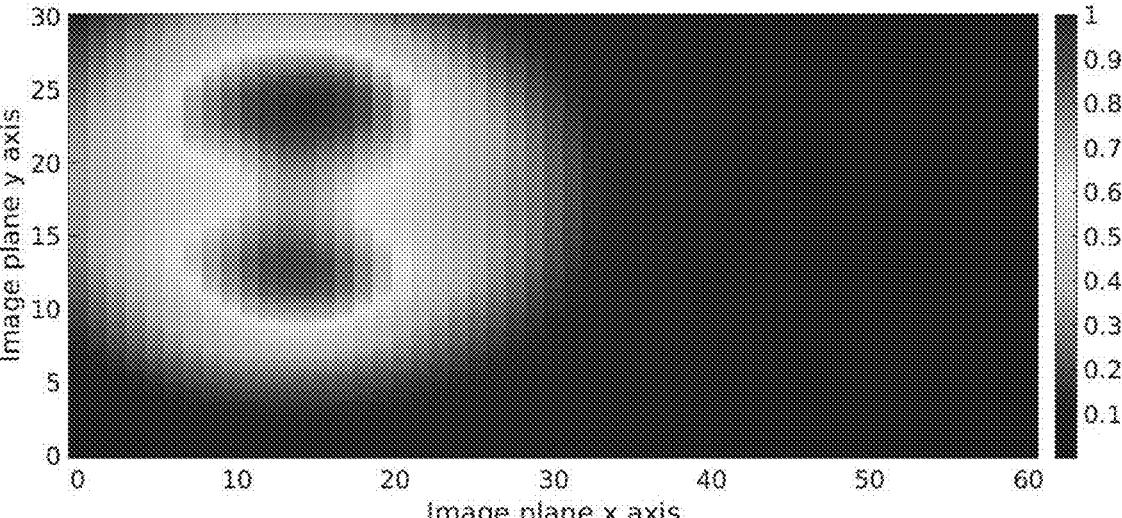
FIG. 6 depicts a radar return image wherein distance is varied to find an optimum distance, in accordance with an embodiment of the present disclosure.
Figure 7:
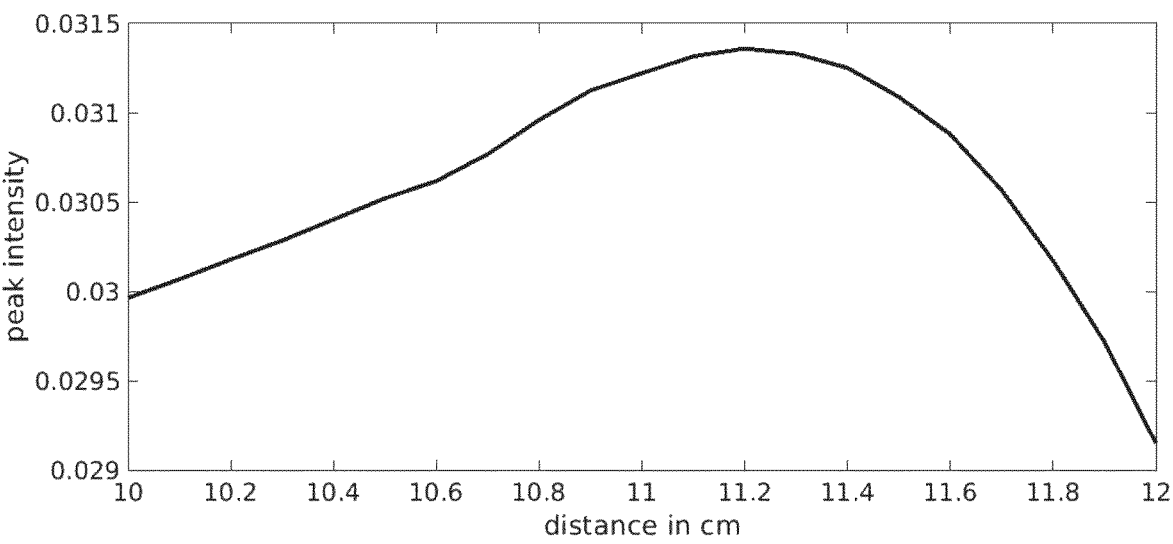
FIG. 7 depicts a graphical representation illustrating a (physical distance) and a region indicating the optimum distance at which the peak intensity is maximum, in accordance with an embodiment of the present disclosure.

At step 212 of the method of the present disclosure, the one or more hardware processors 104 obtain an optimum distance by varying the distance ('d') at which the peak intensity is maximum. The distance d is varied to find the optimum distance $d_{elec}$ in meters at which peak intensity is maximum. FIG. 6, with reference to FIGS. 1 through 5, depicts the radar return image wherein distance is varied to find the optimum distance, in accordance with an embodiment of the present disclosure. FIG. 7, with reference to FIGS. 1 through 6, depicts a graphical representation illustrating a (physical distance) and a region indicating the optimum distance at which the peak intensity is maximum, in accordance with an embodiment of the present disclosure. As can be seen from FIG. 7, the physical distance is around 'x' cm, and distance at which the peak intensity is maximum is 'y' cm. More specifically value of 'x' is 10 cm, and value of 'y' is 11.2 cm indicating maximum peak intensity.

At step 214 of the method of the present disclosure, the one or more hardware processors 104 compute a measured distance based on a comparison between the optimum distance and the initial distance. The measured distance $d_{meas}$ is computed by taking a difference between $d_{elec}$ and $d_{phy}$, in one example embodiment. It is to be understood by a person having ordinary skill in the art or person skilled in the art that such computation of measured distance $d_{meas}$ by taking a difference between $d_{elec}$ and $d_{ph}$, shall not be construed as limiting the scope of the present disclosure.

Figure 8A:
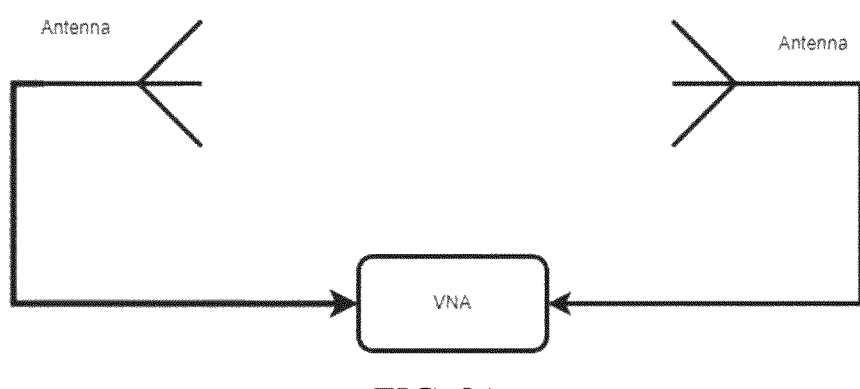
FIG. 8A depicts a first scenario illustrating a method of measuring a second reflection coefficient without placing the DUT between the one or more antennas, in accordance with an embodiment of the present disclosure.
Figure 8B:
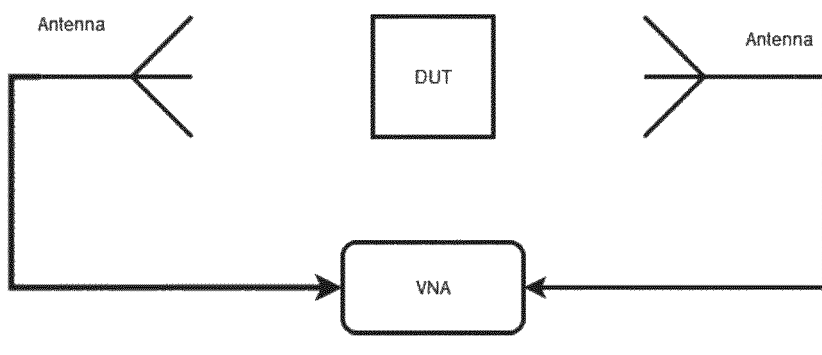
FIG. 8B depicts a second scenario illustrating a method of measuring the third reflection coefficient by placing the DUT between the one or more antennas, in accordance with an embodiment of the present disclosure.

At step 216 of the method of the present disclosure, the one or more hardware processors 104 measure, by using (or via) the VNA, a second reflection coefficient specific to a first scenario and a third reflection coefficient specific to a second scenario. As the first reflection coefficient is measured in step 204, similarly the second reflection coefficient $S_{21\_CAL}$, and the third reflection coefficient $S_{21\_DUT}$ are computed/measured (both are complex values in nature, for instance, in the form of (a+ib)). The first scenario includes measuring the second reflection coefficient without placing the DUT between the one or more antennas, in one example embodiment. The second scenario includes measuring the third reflection coefficient by placing the DUT between the one or more antennas, in one example embodiment. The first scenario may also be referred to as 'first experimental setup' or 'first experimental arrangement' and interchangeably used herein. The second scenario may also be referred to as 'second experimental setup' or 'second experimental arrangement' and interchangeably used herein. FIG. 8A, with reference to FIGS. 1 through 7, depicts a first scenario illustrating a method of measuring the second reflection coefficient without placing the DUT between the one or more antennas, in accordance with an embodiment of the present disclosure. FIG. 8B, with reference to FIGS. 1 through 8A, depicts a second scenario illustrating a method of measuring the third reflection coefficient by placing the DUT between the one or more antennas, in accordance with an embodiment of the present disclosure.

At step 218 of the method of the present disclosure, the one or more hardware processors 104 iteratively perform a plurality of steps (218a through 218c), until a candidate effective permittivity is obtained for each of the plurality of frequencies. More specifically, at step 218a of the method of the present disclosure, the one or more hardware processors 104 compute a permittivity for a plurality of frequencies based on a thickness of DUT, using the second reflection coefficient and the third reflection coefficient. At step 218b of the method of the present disclosure, the one or more hardware processors 104 perform a first comparison of the permittivity with a first threshold. More specifically, the first comparison is between the permittivity with the first threshold. At step 218c of the method of the present disclosure, the one or more hardware processors 104 perform a second comparison of a degree of the DUT with convergence criteria. More specifically, the second comparison is between the degree of the DUT and the convergence criteria. The above steps 218a through 218c are better understood by way of following description.

The below values are considered by way of illustrative examples, and such values shall not be construed as limiting the scope of the present disclosure. $d_{phy}$=10 cm, $d_{elec}$=1.2 cm, $d_{meas}$=1.2 cm, thickness of DUT=1.85 cm, CFseed=1, and convergence criteria (CC) in degrees=7.

For each particular frequency freqz in frequency the following is calculated. Firstly, a ratio is computed based on the second reflection coefficient $S_{21\_CAL}$, and the third reflection coefficient $S_{21\_DUT}$ as $$\text{ratio} = \frac{\text{S21\_DUT}}{\text{S21\_CAL}}.$$

Further, a first variable $\alpha'$ is computed as an absolute value of the ratio, wherein $\alpha'=\text{abs(ratio)}$. Similarly, a second variable $\beta'$ is computed as: $\beta'=\text{abs(angle(ratio))}$. Further, $\alpha'_{dBm}$ is computed as $$\alpha'_{dBm} = \text{abs}\left(\frac{20\log10(\alpha')}{\text{thick}}\right)$$

in dB/m, and $\alpha_{npm}$ is computed as $$\alpha_{npm} = \left(\frac{\text{abs}(\alpha'_{dBm})}{8.68}\right)$$

in Nepers/m. Further, $\beta_{radm}$ is computed as $$\beta_{radm} = \left(\frac{\beta'}{\text{thickness of } DUT}\right).$$

CF (where CF is referred to as correction factor. Seed/initial value of correction factor (CFseed) for a given material is provided as an input to the above calculation. CF is assigned CFseed. A third variable $\Omega_{c0}$ is computed as $$\Omega_{c0} = \left(\frac{2 \cdot \pi \cdot freqz \cdot 10}{3}\right)^2.$$

A fourth variable var1 is computed as $\text{var1}=-(\alpha_{npm}^2-\beta_{radm}^2)$. Further, $$\varepsilon_{eff'} = \left(\frac{\text{var1}}{\Omega_{c0}}\right)$$

is computed which is permittivity. Further, product of $\alpha$ and $\beta$ ($\alpha\beta$) is computed as $\alpha\beta=2\cdot\alpha_{npm}\cdot\beta_{radm}$. A fifth variable var2 is computed $\text{var2}=2\cdot\pi\cdot10^9\cdot4\cdot\pi\cdot10^{-7}\cdot freqz$. Furthermore, a sixth variable sigma is computed as $$\text{sigma} = \left(\frac{\alpha\beta}{\text{var2}}\right).$$

A seventh variable var3 is computed as $\text{var3}=2\cdot\pi\cdot10^9\cdot8.854.10^{-12}\cdot\varepsilon_{eff}$. Moreover, an eight variable $\tan\theta'$ is computed as $$\tan\theta' = \left(\frac{\text{sigma}}{\text{var3}}\right).$$

A nineth variable $\lambda_g$ is computed as $$\lambda_g = \frac{3\cdot10^8}{freqz\cdot10^9\sqrt{\varepsilon_{eff'}}}$$

wavelength in meters. A tenth variable $\beta_{path}$ is computed as $$\beta_{path} = \left(\frac{2\cdot\pi\cdot\text{thick}}{\lambda_g}\right).$$

An eleventh variable $\beta_{diffrad}$ is computed as $\beta_{diffrad}=\beta'-\beta_{path}$ in radians. Finally, a twelfth variable $\beta_{diff}$ is computed as $$\beta_{diff} = \left(\frac{\beta_{diffrad}\cdot180}{\pi}\right)$$

in degrees. The absolute value of $\beta_{diff}$ is referred to as degree of DUT. As mentioned above, the permittivity $\varepsilon_{eff}$ is compared with the first threshold. In the present disclosure, as per the experiments conducted and described herein, the first threshold is 1. Therefore, value of the permittivity $\varepsilon_{eff}$ is compared with 1 to determine whether it is less than or equal to or greater than 1. If the permittivity $\varepsilon_{eff}$ is less than 1, then the step 218a is repeated with a different $CF_{seed}$ value. Else, if the permittivity $\varepsilon_{eff}$ is not less than 1 or greater than 1, then the absolute value of $\beta_{eff}$ is compared with the convergence criteria. The above check or comparison is repeated until the absolute value of $\beta_{diff}$ is greater than or equal to the first threshold (in this case 1). For instance, a check is performed by the system 100 and the method of the present disclosure whether the $\text{abs}(\beta_{diff})>CC$. If the absolute value of $\beta_{diff}$ is greater than the CC which in this case is 7, then the value of CF is incremented by 0.001 and then the step of comparing the absolute value of $\beta_{diff}$ with the convergence criteria is repeated. This check or comparison and incrementing the value of CF happens until the absolute value of $\beta_{diff}$ is less than or equal to the value of the CC. Once, both the conditions are satisfied, then a candidate effective permittivity for each frequency is obtained. In other words, a plurality of candidate effective permittivity are obtained. The value of $\varepsilon_{eff}$ for the corresponding freqz is stored in the database 108 or memory 102 of the system 100. If all the frequency check is not completed, a next value in frequency is selected as freqz and the step of comparing the absolute value of $\beta_{diff}$ with the convergence criteria is repeated with CF=CFseed. As can be seen from the steps 218a through 218c, the permittivity is iteratively computed until the comparison conditions of 218b and 218c are satisfied. In other words, such iterative computation is also referred to as an iterative search method as known in the art.

At step 220 of the method of the present disclosure, the one or more hardware processors 104 compute an effective permittivity based on the candidate effective permittivity computed for each of the plurality of frequencies. In other words, using the plurality of candidate effective permittivity, the effective permittivity is computed. The effective permittivity $\varepsilon_{eff}$ is computed as $\varepsilon_{eff}=\text{average}(\varepsilon_{eff})$. More specifically, the average of the plurality of candidate effective permittivity is taken to obtain the effective permittivity $\varepsilon_{eff}$. It is to be understood by a person having ordinary skill in the art or person skilled in the art that such computation of the effective permittivity $\varepsilon_{eff}$ by taking the average of the plurality of candidate effective permittivity shall not be construed as limiting the scope of the present disclosure. In other words, the system and method of the present disclosure may employ any other logical or mathematical operation on the average of the plurality of candidate effective permittivity to obtain the effective permittivity $\varepsilon_{eff}$.

At step 222 of the method of the present disclosure, the one or more hardware processors 104 compute at least one of an actual depth and an actual diameter of an anomaly in the biological tissue based on the measured distance $d_{meas}$ and the effective permittivity $\varepsilon_{eff}$. The actual depth ($d_{act}$) of the anomaly in the biological tissue is computed by way of following expression:

$$d_{act} = \frac{dmeas}{\sqrt{\varepsilon_{eff}}}.$$

Figure 9:
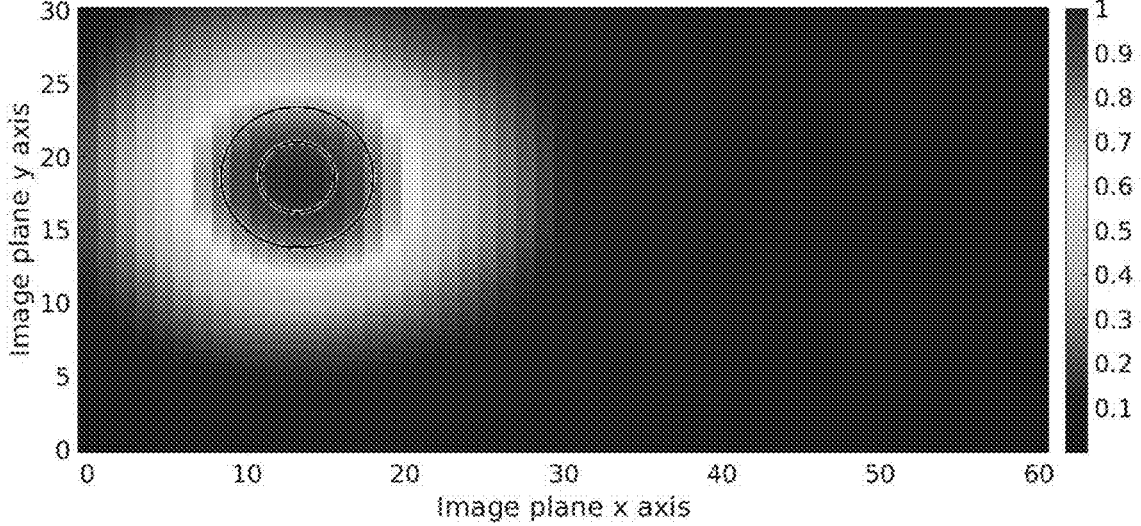
FIG. 9 depict the anomaly in the biological tissue with various diameters being computed, in accordance with an embodiment of the present disclosure.

It is to be understood by a person having ordinary skill in the art or person skilled in the art that such computation of the actual depth ($d_{act}$) as shown above shall not be construed as limiting the scope of the present disclosure. In other words, the system and method of the present disclosure may employ any other logical or mathematical operation on the measured distance $d_{meas}$ and the effective permittivity $\varepsilon_{eff}$ to compute the actual depth ($d_{act}$). FIG. 9, with reference to FIGS. 1 through 8B, depict the anomaly in the biological tissue with various diameters being computed, in accordance with an embodiment of the present disclosure. In the present disclosure, the system and method through the experiments conducted (not shown), computed inner circle diameter as 9.8 cm (90%), outer circle diameter as 9.6 cm (80%), and actual diameter as 2.4 cm. The actual depth has been computed as actual depth ($d_{act}$)=0.7 cm. It is to be understood by a person having ordinary skill in the art or person skilled in the art that the above computation of the actual depth and the actual diameter of the anomaly in the biological tissue shall not be construed as limiting the scope of the present disclosure, and such computation value of the actual depth and the actual diameter of the anomaly in the biological tissue vary based on the type of biological tissue and the environment of the experimental setup/arrangement.

Existing techniques do not consider the detection, characterization of anomaly in biological tissues which lead to dielectric imaging in this way, where the imaging plane and physical plane are different. Thus, most of the conventional techniques are not suitable for in-vivo applications. Embodiments of the present disclosure provide systems and methods for anomaly detection in biological tissues in the BMWI framework. An intensity map of the target region is generated to detect the tumor. Then the area around the tumor is further processed to obtain the refined image. As the tumor is embedded in tissues of higher dielectric constant, the image thus formed is usually larger in size than the actual tumor. Thus, to estimate the accurate size, the system of the present disclosure implements an iterative numerical computation method to estimate relative permittivity ($\varepsilon r$). Subsequently, the effective size of the anomaly is approximately estimated, which is close to their actual values.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
receiving, at a Vector Network Analyzer (VNA) via one or more hardware processors, one or more reflected microwaves projected on a duty under test (DUT) kept at an initial distance, by using one or more antennas, wherein the DUT comprises a biological tissue;
measuring, by using the VNA via the one or more hardware processors, a first reflection coefficient from the one or more reflected microwaves;
converting, via the one or more hardware processors, the first reflection coefficient to a time series data and filtering the time series data to obtain a filtered time series data;
applying, a Delay-Multiply-and-Sum (DMAS) technique via the one or more hardware processors, on the filtered time series data to generate a radar return image at a distance from a frontend of the one or more antennas;
measuring, via the one or more hardware processors, a peak intensity from the radar return image;
obtaining, via the one or more hardware processors, an optimum distance by varying the distance at which the peak intensity is maximum;
computing, via the one or more hardware processors, a measured distance based on a comparison between the optimum distance and the initial distance;
measuring, by using the VNA via the one or more hardware processors, a second reflection coefficient specific to a first scenario and a third reflection coefficient specific to a second scenario;
iteratively performing, via the one or more hardware processors:
    computing a permittivity for a plurality of frequencies based on a thickness of DUT, using the second reflection coefficient and the third reflection coefficient;
    performing a first comparison of the permittivity with a first threshold; and
    performing a second comparison of a degree of the DUT with a convergence criteria,
    until a candidate effective permittivity for each of the plurality of frequencies is obtained based on the first comparison and the second comparison;
computing, via the one or more hardware processors, an effective permittivity based on the candidate effective permittivity computed for each of the plurality of frequencies; and
computing, via the one or more hardware processors, at least one of an actual depth and an actual diameter of an anomaly in the biological tissue based on the measured distance and the effective permittivity.

2. The processor implemented method of claim 1, wherein the filtering of the time series data to obtain the filtered time series data is based on a second threshold.

3. The processor implemented method of claim 2, wherein the second threshold is a pre-configured threshold or an empirically determined threshold.

4. The processor implemented method of claim 1, wherein the first scenario comprises measuring the second reflection coefficient without placing the DUT between the one or more antennas, and the second scenario comprises measuring the third reflection coefficient by placing the DUT between the one or more antennas.

5. The processor implemented method of claim 1, wherein the step of computing the permittivity is based on an iterative search method.

6. A system, comprising:
a memory storing instructions;
one or more communication interfaces; and
one or more hardware processors coupled to the memory via the one or more communication interfaces, wherein the one or more hardware processors are configured by the instructions to:
receive, at a Vector Network Analyzer (VNA), one or more reflected microwaves projected on a duty under test (DUT) kept at an initial distance, by using one or more antennas, wherein the DUT comprises a biological tissue;
measure, by using the VNA, a first reflection coefficient from the one or more reflected microwaves;
convert the first reflection coefficient to a time series data and filtering the time series data to obtain a filtered time series data;
apply a Delay-Multiply-and-Sum (DMAS) technique on the filtered time series data to generate a radar return image at a distance from a frontend of the one or more antennas;
measure a peak intensity from the radar return image;
obtain an optimum distance by varying the distance at which the peak intensity is maximum;
compute a measured distance based on a comparison between the optimum distance and the initial distance;
measure, by using the VNA, a second reflection coefficient specific to a first scenario and a third reflection coefficient specific to a second scenario;
iteratively perform:
    computing a permittivity for a plurality of frequencies based on a thickness of DUT, using the second reflection coefficient and the third reflection coefficient;
    performing a first comparison of the permittivity with a first threshold; and
    performing a second comparison of a degree of the DUT with a convergence criteria,
    until a candidate effective permittivity for each of the plurality of frequencies is obtained based on the first comparison and the second comparison;
compute an effective permittivity based on the candidate effective permittivity computed for each of the plurality of frequencies; and
compute at least one of an actual depth and an actual diameter of an anomaly in the biological tissue based on the measured distance and the effective permittivity.

7. The system of claim 6, wherein the filtered time series data is based on a second threshold.

8. The system of claim 7, wherein the second threshold is a pre-configured threshold or an empirically determined threshold.

9. The system of claim 6, wherein the first scenario comprises measuring the second reflection coefficient without placing the DUT between the one or more antennas, and the second scenario comprises measuring the third reflection coefficient by placing the DUT between the one or more antennas.

10. The system of claim 6, wherein the permittivity is computed based on an iterative search method.

11. One or more non-transitory machine-readable information storage mediums comprising one or more instructions which when executed by one or more hardware processors cause:

receiving, at a Vector Network Analyzer (VNA), one or more reflected microwaves projected on a duty under test (DUT) kept at an initial distance, by using one or more antennas, wherein the DUT comprises a biological tissue;

measuring, by using the VNA, a first reflection coefficient from the one or more reflected microwaves;

converting the first reflection coefficient to a time series data and filtering the time series data to obtain a filtered time series data;

applying, a Delay-Multiply-and-Sum (DMAS) technique, on the filtered time series data to generate a radar return image at a distance from a frontend of the one or more antennas;

measuring a peak intensity from the radar return image;

obtaining an optimum distance by varying the distance at which the peak intensity is maximum;

computing a measured distance based on a comparison between the optimum distance and the initial distance;

measuring, by using the VNA, a second reflection coefficient specific to a first scenario and a third reflection coefficient specific to a second scenario;

iteratively performing:

computing a permittivity for a plurality of frequencies based on a thickness of DUT, using the second reflection coefficient and the third reflection coefficient;

performing a first comparison of the permittivity with a first threshold; and performing a second comparison of a degree of the DUT with a convergence criteria, until a candidate effective permittivity for each of the plurality of frequencies is obtained based on the first comparison and the second comparison;

computing an effective permittivity based on the candidate effective permittivity computed for each of the plurality of frequencies; and computing, at least one of an actual depth and an actual diameter of an anomaly in the biological tissue based on the measured distance and the effective permittivity.

12. The one or more non-transitory machine-readable information storage mediums of claim 11, wherein the filtering of the time series data to obtain the filtered time series data is based on a second threshold.

13. The one or more non-transitory machine-readable information storage mediums of claim 12, wherein the second threshold is a pre-configured threshold or an empirically determined threshold.

14. The one or more non-transitory machine-readable information storage mediums of claim 11, wherein the first scenario comprises measuring the second reflection coefficient without placing the DUT between the one or more antennas, and the second scenario comprises measuring the third reflection coefficient by placing the DUT between the one or more antennas.

15. The one or more non-transitory machine-readable information storage mediums of claim 11, wherein the step of computing the permittivity is based on an iterative search method.

\* \* \* \* \*